United States Patent
Parkin et al.

(12)

(10) Patent No.: US 6,235,039 B1
(45) Date of Patent: May 22, 2001

(54) SKIN ABRASION DEVICE

(76) Inventors: Roger C. Parkin, 15 Springton Point Dr., Newtown Sq., PA (US) 19073; George Maguire, 104 Campbell Dr., Conshohocken, PA (US) 19428

( * ) Notice: Subject to any disclaimer, the term of this patent is extended or adjusted under 35 U.S.C. 154(b) by 0 days.

(21) Appl. No.: 09/496,394

(22) Filed: Feb. 2, 2000

Related U.S. Application Data

(63) Continuation-in-part of application No. 09/255,954, filed on Feb. 23, 1999.

(51) Int. Cl.[7] .................................................. A61B 17/50
(52) U.S. Cl. ................................................................ 606/131
(58) Field of Search .................... 606/131–133; 433/88; 604/35; 601/161

(56) References Cited

U.S. PATENT DOCUMENTS

| | | | |
|---|---|---|---|
| 3,974,833 | 8/1976 | Durden, III | 128/275.1 |
| 5,037,432 | * 8/1991 | Molinari | 606/131 |
| 5,100,412 | 3/1992 | Rosso | 606/131 |
| 5,207,234 | 5/1993 | Rosso | 128/898 |
| 5,460,604 | * 10/1995 | Arnett et al. | 606/161 |
| 5,470,305 | * 11/1995 | Arnett et al. | 606/161 |
| 5,562,643 | 10/1996 | Johnson | 604/290 |
| 5,674,235 | 10/1997 | Parisi | 606/169 |
| 5,807,386 | 9/1998 | Slatkine et al. | 606/9 |
| 5,954,730 | 9/1999 | Bernabei | 606/131 |
| 5,971,999 | * 10/1999 | Naldoni | 606/131 |
| 6,036,684 | 3/2000 | Takovich et al. | 606/9 |
| 6,039,745 | 3/2000 | Di Fiore et al. | 606/131 |

FOREIGN PATENT DOCUMENTS

| | | |
|---|---|---|
| 0564392 | 10/1993 | (EP) . |
| 0324448 | 3/1995 | (EP) . |
| 0806184 | 11/1997 | (EP) . |
| 2712172 | 5/1995 | (FR) . |
| 9700050 | 1/1997 | (WO) . |
| 9711650 | 4/1997 | (WO) . |
| 9923951 | 5/1999 | (WO) . |
| 0002602 | 1/2000 | (WO) . |

OTHER PUBLICATIONS

Ravi Pachigolla, M.D., "Dermabrasion And Chemical Peels", Grand Rounds of the UTMB Department of Otolaryngology, Jan. 8, 1997.

Hard copy printout of Internet www pages from Permark web site, 5 pages, URL is http://www.permark.com, download date of May 19, 2000.

Hard copy printout of Internet www pages from Dermabraders web site, 5 pages, URL is http://www.justinscientific.com, download date of May 23, 2000.

Hard copy printout of Internet www pages from Derma Genesis web site, 3 pages, URL is http://www.dermagenesis.com, download date of May 19, 2000.

* cited by examiner

*Primary Examiner*—Kevin Truong
(74) *Attorney, Agent, or Firm*—Ostrolenk, Faber, Gerb & Soffen, LLP

(57) ABSTRACT

A novel handpiece and system for abrasion of skin is disclosed. A short handpiece with a threadably removable tip is used. The opening in the tip is centered on the handpiece axis and a small diameter particle inlet channel and larger diameter outlet channel are both offset from the handpiece axis. A central blade or barrier within the tip divides the tip into two volumes which each communicate with the opening and respective ones of the inlet and outlet passages. A vacuum control opening is formed in the tip for easy control by the operator. Abrasive particles and removed tissue are applied to the interior of a cylindrical filter supported within a supporting container. The annular area between the container and this filter is connected through a secondary emergency filter to a vacuum pump. The cylindrical filter can be a flexible filter bag. A large source of abrasive particles is coupled to the handpiece inlet and the filter is coupled to the handpiece outlet.

20 Claims, 6 Drawing Sheets

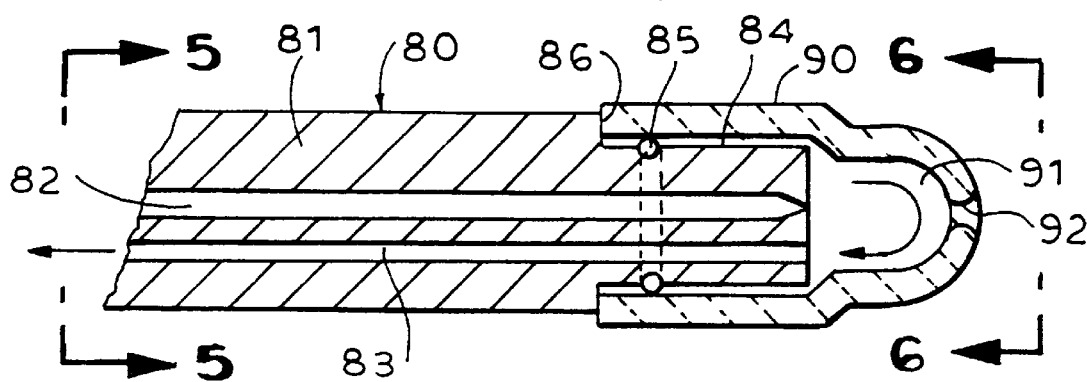
*Fig. 4.* PRIOR ART
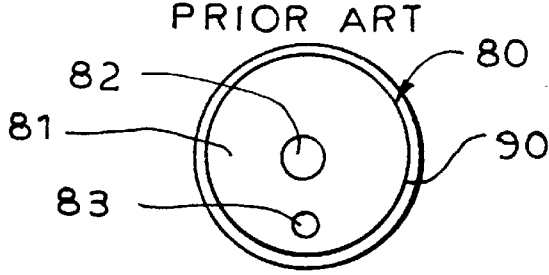
*Fig. 5.* PRIOR ART
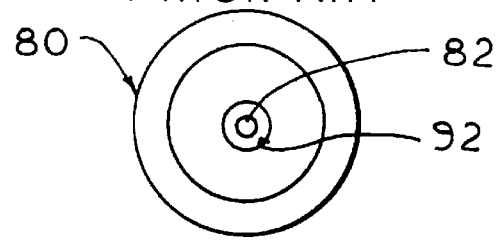
*Fig. 6.* PRIOR ART
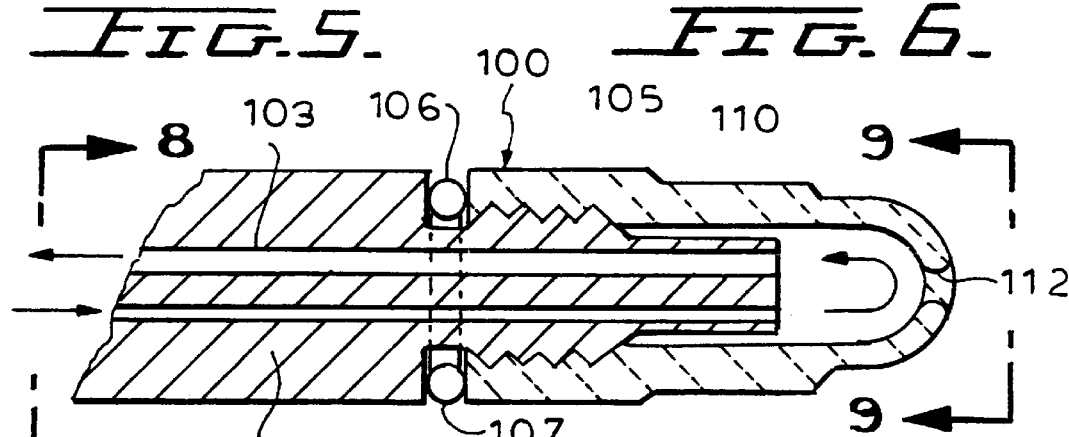
*Fig. 7.*
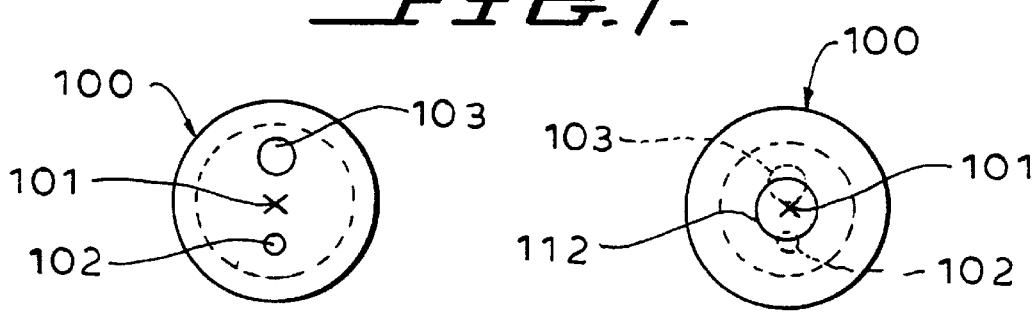
*Fig. 8.*    *Fig. 9.*

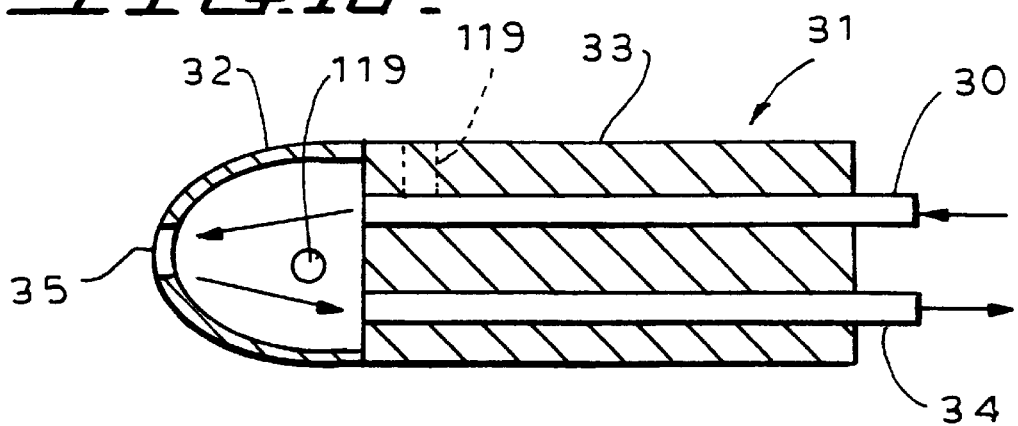
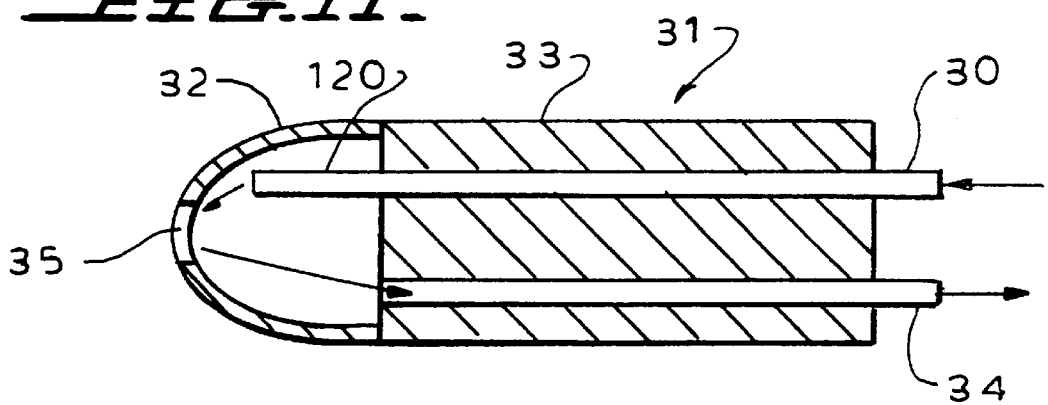
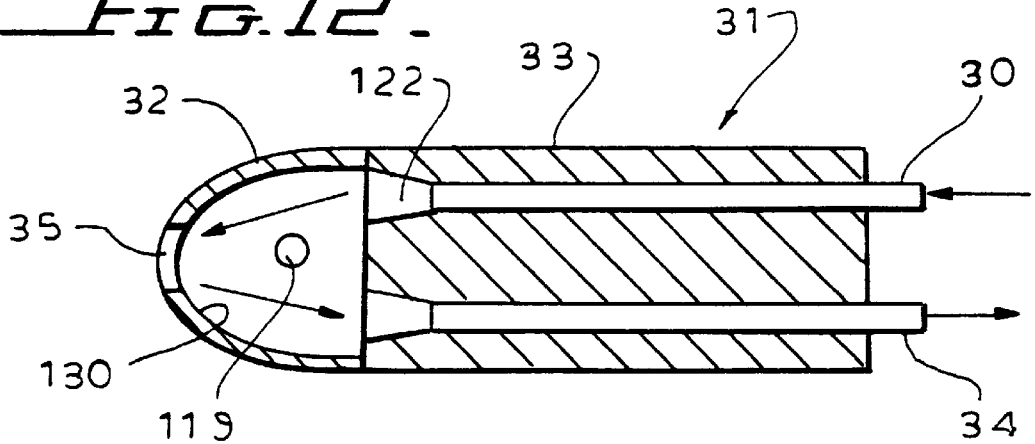

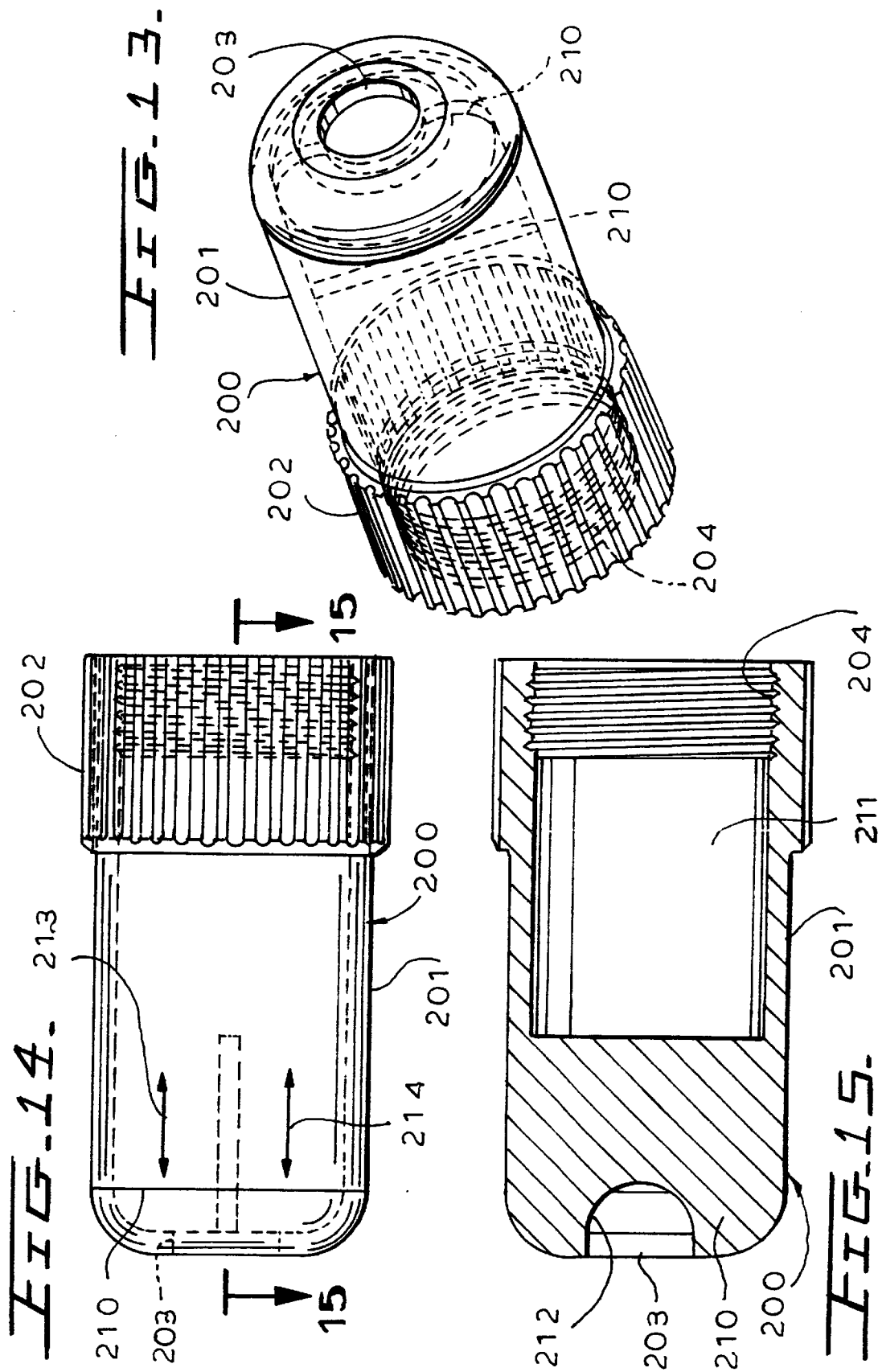

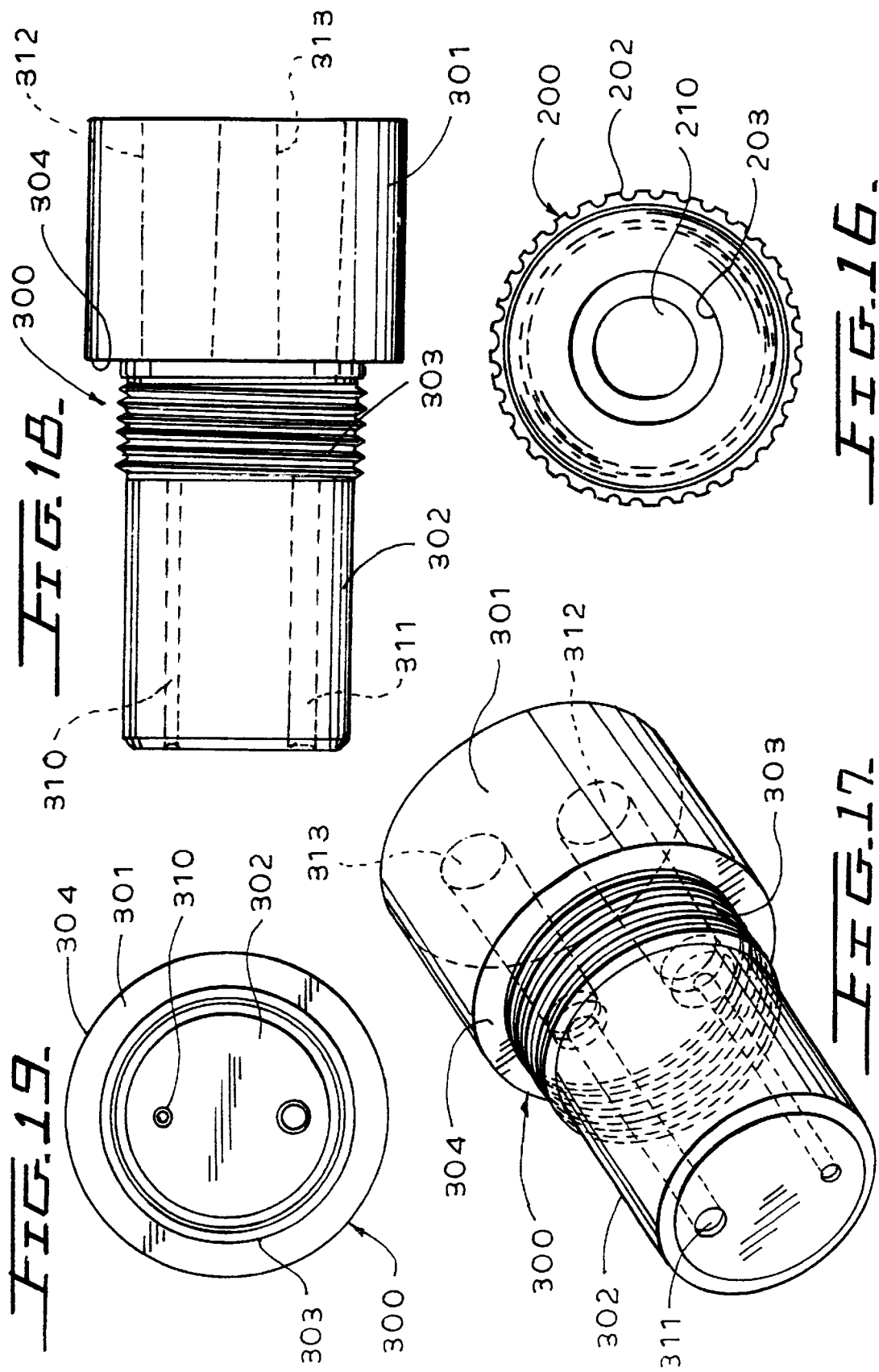

SKIN ABRASION DEVICE

RELATED APPLICATIONS

This application is a continuation-in-part of copending application Ser. No. 09/255,954 filed Feb. 23, 1999 now pending.

FIELD OF THE INVENTION

This invention relates to the removal of surface portions of dead or living tissue, sometimes termed microdermal abrasion and more specifically relates to an improved apparatus and process for the abrasion of surface portions of human tissue by the controlled flow of abrasive particles.

BACKGROUND OF THE INVENTION

Apparatus for the microdermal abrasion of the surface of tissue (living or dead) is well known. In these processes, a stream of abrasive particles such as sand is applied to the surface of the tissue or skin through an opening in a hand held tool (termed a handpiece) which is sealed against the skin. The tool and the particle stream is controllably scanned over the area to be abraded. The abrading particles and the removed tissue are then collected by vacuum in the handpiece and are passed through and collected by a filter to prevent the escape of the abraded tissue and sand into the vacuum pump and ambient atmosphere.

The handpiece has taken many forms in the past but usually provides a first passage for conducting abrasive particles from a reservoir to the area to be treated and a second parallel channel for conducting the particles and abraded skin away from the area treated and into a disposal vessel.

A typical prior art apparatus is shown in U.S. Pat. No. 5,037,432. The hand-held head of this patent is a long tubular structure having an off-center hole which permits the application of an abrasive particle jet to an area to be treated, and the subsequent removal of the particles and abraded skin. The off-center outlet hole is arranged to be on the same axis as the input abrasive particle jet which then reaches the area to be treated at a 45° angle. The outlet jet channel facing the opening has a nozzle restriction. The abraded skin and used particles are then withdrawn through a parallel return vacuum channel which is connected to a vacuum pump through a filter.

The above described hand held tool has a number of drawbacks. Thus, because it is relatively long (longer than about 5 inches) it is difficult to manipulate easily over a curved surface area to be abraded, for example, the surface of a human face. Further, the vacuum pressure within the hand tool is not easily changed by the operator when a weaker or more forceful jet of abrasive particles is desired at particular locations on the surface area being abraded. Further, the handpiece is subject to clogging at the restricted outlet nozzle, requiring the operator frequently to stop the treatment and clear the nozzle.

The above described handpiece is provided with a removable and disposable tip or bell section which contains the output hole. Thus, the tip can be removed and disposed of and replaced by a new tip after the treatment of each individual. The tip is normally press-fit onto the body of the handpiece and is tightly sealed thereto to prevent accidental escape of abraded skin and loss of vacuum. Therefore, the tip is very difficult to remove and replace.

It would be very desirable to provide a handpiece for abrasion of living tissue which avoids the above problems.

The abrasive particles and tissue which are removed in prior art devices are collected in a filter placed between the handpiece outlet channel and the vacuum pump. Such a filtration system is shown in U.S. Pat. Nos. 5,100,412 and 5,207,234 in the name of Rosso. The filter shown therein is an inverted cup at the outlet opening of a waste receiving chamber. The outlet opening is connected to the vacuum pump line and contaminated particles and debris flow from the cup exterior toward its interior thus building up on the cup exterior. This filter tends to become quickly clogged and becomes more and more impervious to the flow of air therethrough. Consequently, the system must be frequently turned off and the filter must be cleaned sometimes during and frequently after each use.

It would be very desirable to provide a filtration system which does not require frequent cleaning or emptying.

SUMMARY OF THE INVENTION

In accordance with the invention a novel apparatus and process is provided which avoids the problems with prior art devices as stated above, and which provides added improved operation as well.

In accordance with a first feature of the invention, a novel filtration system is provided in which a large area cylindrical filter is disposed coaxially within a large volume container with an annular air outlet chamber defined between the cylindrical filter and the container. The annular outlet channel is connected to the vacuum pump of the system.

In operation, abrasion particles and skin are conveyed from the outlet channel of the hand held instrument to the interior of the cylindrical filter and are then entrapped within the large surface area interior of the filter. Filtered air then passes through the filter and into the annular low pressure area surrounding the filter and then into the vacuum pump. Because of the large area of the filter, it need not be replaced frequently and will commonly not require replacement until after about 50 uses (or 50 patient treatments).

A back-up emergency filter is coupled between the annular filter volume and vacuum pump to prevent the flow of abrasion particles to the pump in the event of a failure or accidental bypass of the main filter.

The novel cylindrical filter may be mounted between top and bottom flexible disks or flanges which have a larger diameter than the cylindrical filter to permit the easy and rapid replacement of a new filter assembly after a given time or number of operations. The used sand and removed tissue will be trapped within the filter and between the gaskets during this operation. Note that the gaskets may have connection nipples or simple connection openings for input and output conduits which enter the filter interior and annular chamber respectively.

As an alternative to the above cylindrical filter which is rigid, it is also possible to employ a removable paper bag type of filter which is clamped around the inlet conduit, providing similar benefits to those described above at lower cost.

A novel hand-held head or handpiece is also provided with a novel modified design from that of the prior art.

As a first feature of the novel handpiece, a screw-on tip of clear plastic is used which makes threaded engagement with the body of the tool. Thus the tip is easily removed from and replaced on the handpiece body after a single use. The tip is hemispherical in shape and has a sand-blast opening on its central axis. Sand input and output channels in the body extend parallel to the central axis and the axis of the tip and are displaced toward opposite sides of the central axis. Thus, the opening in the tip is on the central axis of the tool body but is displaced from the input and output channels. The sand will then sweep past the opening (and skin adjacent thereto) in its travel within the tip to abrade the skin. Moreover, the diameter of the sand input channel to the tip interior is relatively smaller than the output vacuum channel (for example, 1/16 inch versus 1/8 inch respectively). This enables the quicker and easier withdrawal of used sand and skin particles from the interior vacuum chamber formed between the end of the body and the tip and aids in prevention of leakage of sand from the skin area being treated if the tip is removed from the area having treated. Note that in use, the hole in the tip is sealed against the skin area to preserve the vacuum and sand flow within the tip.

As a further feature of the novel handpiece, the entire body is shortened to a length less than about 3 inches. This makes it much easier to manipulate the tip over the surface being treated.

As a still further feature of the new handpiece, a small opening is provided in the side of the tip which can be easily covered by the finger of the operator. Thus, the vacuum pressure within the tip can be immediately changed by the operator without having to reach for the main pressure control at the main housing to which the handpiece is attached. It should be noted that this opening can also be placed in the handpiece body and can communicate with either the inlet or the outlet channel and still accomplish the stated function.

As a still further feature of the handpiece, the end of the channel carrying sand to the tip is not restricted by a nozzle, but is of the same diameter as the input channel or even flared out to a larger diameter to prevent clogging of the input channel. The flare may also be used at the end of the output channel adjacent the tip. It has been found that the elimination of the nozzle does not adversely affect the operation of the system.

As a further feature of the present invention, a novel large volume particle supply reservoir is provided in which, for example, a five pound supply of an abrasive, such as, irregularly shaped aluminum oxide particles of a maximum dimension less than about 120 microns and with sharp irregular edges is stored. A nipple at the bottom of the container is connected to an outlet tube, which in turn is coupled to a particle flow control valve which permits air flow into the conduit to carry the sand around the system with a controlled mass flow. The container can be easily replaced or replenished.

In accordance with an improvement of the present application, the screw-on tip has a central elongated barrier or separator extending along the axis of the tip to its opening to define sand input and outlet chambers along the length of the tip to increase the volume of sand which reaches and abrades the area being treated.

BRIEF DESCRIPTION OF THE DRAWING(S)

FIG. 4 is a cross-sectional view of a prior art handpiece.

FIG. 5 is an end view of the handpiece of FIG. 4 as seen from line 5—5 in FIG. 4.

FIG. 6 is a sectional view of the handpiece of FIG. 4 as seen from line 6—6 in FIG. 4.

FIG. 7 is a cross-sectional view of a novel handpiece containing many of the features of the present invention.

FIG. 8 is a sectional view of the handpiece of FIG. 7 as seen from line 8—8 in FIG. 7.

FIG. 9 is an end view of FIG. 7 as seen from the line 9—9 in FIG. 7.

FIG. 10 schematically shows a novel handpiece which contains a sand velocity control aperture in the tool tip.

FIG. 11 schematically shows a handpiece which contains a sand input channel which extends into the tip interior.

FIG. 12 schematically shows flares at the ends of the input and output channels in the handpiece to prevent clogging.

FIG. 13 is a perspective view of a preferred embodiment of the tip portion 32/90/110 of the preceding figures.

FIG. 14 is a side view of the tip portion of FIG. 13.

FIG. 15 is a cross-sectional view of FIG. 14 taken across section line 15—15 in FIG. 14.

FIG. 16 is an end view of FIG. 14.

FIG. 17 is a perspective view of a preferred handpiece for the replaceable tip of FIGS. 13 to 16.

FIG. 18 is a side view of the handpiece of FIG. 17.

FIG. 19 is an end view of the handpiece of FIG. 18.

DETAILED DESCRIPTION OF THE INVENTION

Figure 1:
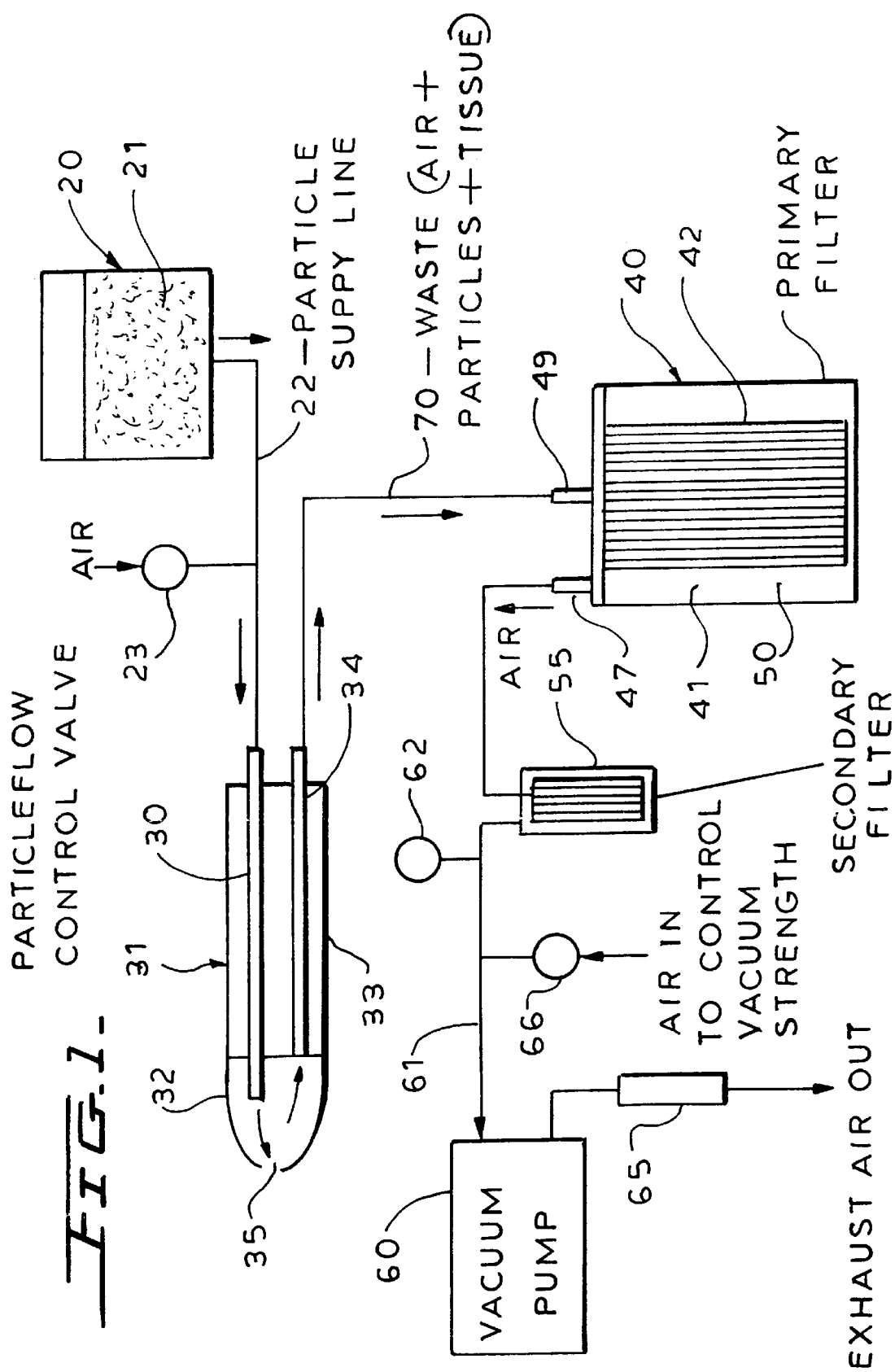
FIG. 1 is a schematic diagram of the novel system of the invention.

Referring first to FIG. 1, there is shown a supply container 20, which can, for example, contain about 5 pounds of a suitable abrasive sand 21, for example, aluminum oxide particles with very sharp edges and a non-critical maximum dimension of about 120 microns. An output particle supply line 22 which may be a plastic conduit of about 1/4 inch O.D. is connected to a suitable connection nipple (not shown) on the bottom of can 20. A particle flow control valve 23 is provided to control the air flow from the atmosphere into supply line 22 to move abrasive particles in the input conduit 30 of handpiece 31; moving sand faster when the valve is closed.

Handpiece 31 further includes a hemispherical shaped tip 32 which is removably connected to body 33. The body 33 contains input channel 30 and output channel 34 which will be later described in detail. Channel 30 conventionally has a diameter of about 1/8 inch and channel 34 is conventionally about 1 inch in diameter.

Removable tip 32 is a hollow hemispheric structure having a diameter of about 1 inch, a length of about 1½ inch, and has a central aperture 35 on its axis. Typically, aperture 35 has a non-critical diameter of 1/4 to 3/8 inch. In use, the aperture 35 is sealed against the surface to be treated and particles from conduit 30 pass by and abrade the skin exposed through aperture 35. The used sand particles and abraded tissue are then removed through channel 34 and are directed to a novel filter 40.

Filter 40 consists of a cylindrical metal container 41 (FIGS. 2 and 3) which may have a 6 inch diameter and contains a cylindrical pleated filter 42 which may be overwrapped with a flat filter paper. A standard 3 pound coffee container has been used for can 41. The filters are sized to ensure trapping of the 120 micron sized particles and the abraded tissue. The cylindrical filter 42 is fixed as by cementing at top and bottom to rubber flange disks 43 and 44 respectively best shown in FIGS. 2 and 3. These may be formed of a silicone rubber about 1/4 inch thick. The top disk 43 has openings 45 and 46 which receive air outlet conduit 47 and an air-plus-particle inlet conduit 48. Conduits 47 and 48 are fused or otherwise sealably connected to openings in disk 43. Conduits 47 and 48 may be flexible plastic tubes with O.D.'s of ⅜ and ¼ inch respectively.

The disks 43 and 44 are press-fitted into the inner diameter of container 41 and can be glued to the container interior. They form a sealed annular chamber 50 which surrounds filter 42 and communicates with conduit 47.

While filter 42 is shown as a rigid filter fixed between rubber disks 43 and 44, it can be replaced by a simple filter bag suitably clamped to input conduit 48.

In operation, waste particles and tissue flow from the handpiece and into filter 42 and are collected therein. Filtered air passes through the filter 42, into the low pressure annular volume 50 and out through conduit 47 toward vacuum pump 60. This filtered air also flows through an secondary back-up filter 55 which prevents flow of abrasive particles into vacuum pump 60 (a ⅓ horse power pump) if filter 40 is accidentally bypassed. A ⅜ inch conduit 61 connects filter 55 to pump 60.

A pressure gauge 62 monitors the pressure at the input to pump 60 (reading from 0 to 100 KPA vacuum). The exhaust air from pump 60 is exhausted to the exterior atmosphere through muffler 65. A valve 66 controls the vacuum in line 61.

It will be noted that valves 23 and 66 along with selected other elements of the system may be housed in a control box (not shown). The filters 40 and 55 and reservoir 20 are suitably mounted for greatest convenience. The handpiece 31 is connected to the particle supply by the elongated and flexible supply line 22, and to the filter 40 by a similar elongated flexible line 70. Lines 22 and 70 ensure that an operator can manipulate the handpiece 31 as necessary for its use.

Figure 2:
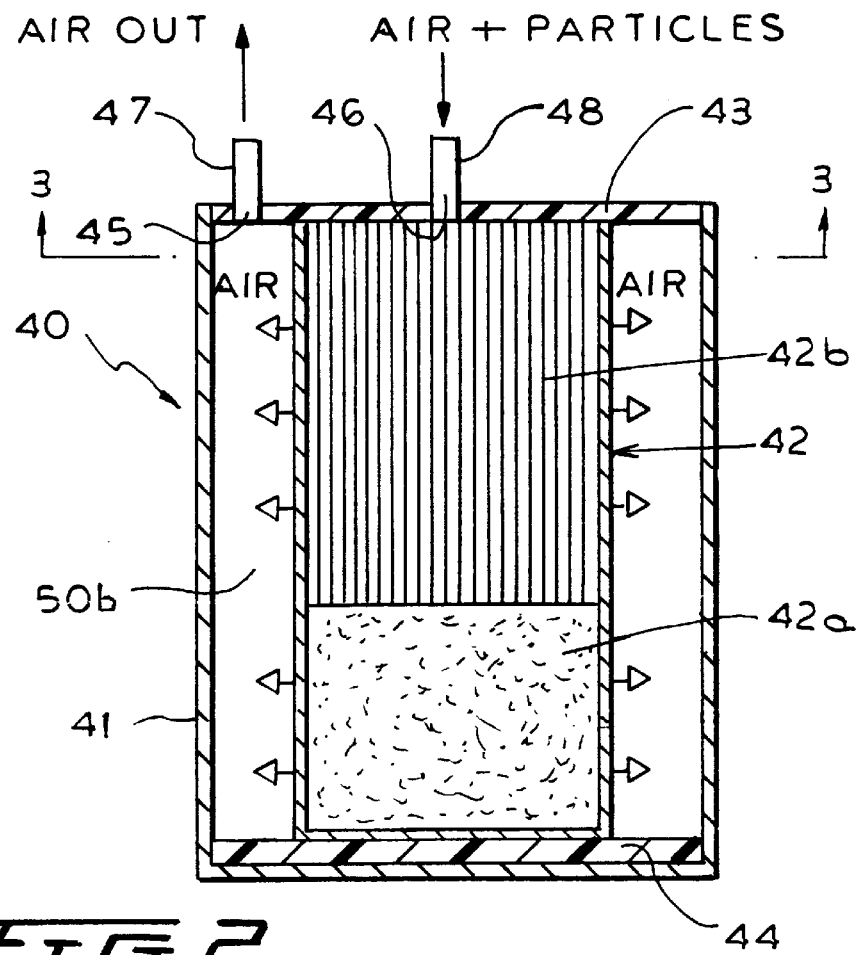
FIG. 2 is a schematic cross-sectional view of the novel filter structure of FIG. 1.
Figure 3:
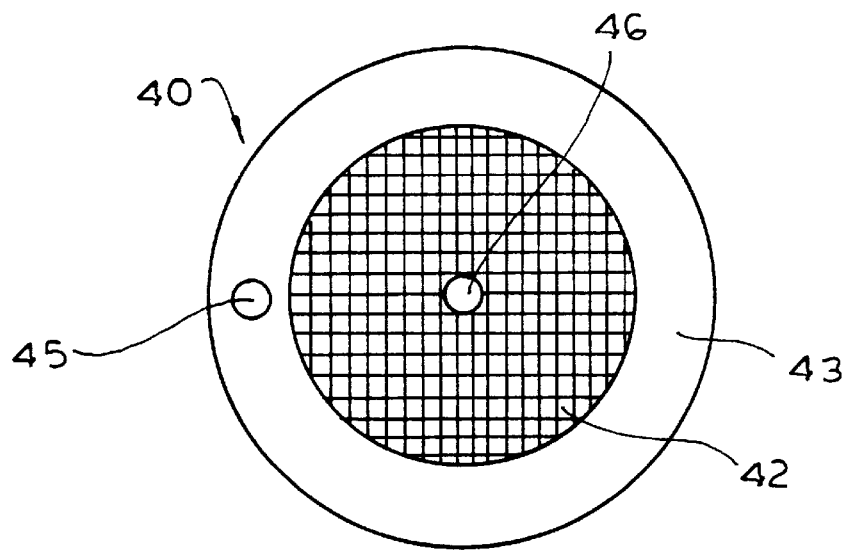
FIG. 3 is a top view of FIG. 2.

FIG. 4, 5 and 6 show a prior art type of handpiece 80 which can be used with the novel filter and system of FIGS. 1, 2 and 3. The handpiece 80 consists of a solid plastic body 81 having a large diameter channel 82 which is coaxial with the axis of body 81 and a smaller diameter outflow channel 83. A restrictive nozzle is commonly placed at the end of channel 82. Body 80 has a length of about 5 inches and a reduced diameter end section 84, about 1 inch long. An O-ring gasket 85 is fixed around the diameter of section 84, at a point removed from the shoulder 86. A rigid transparent plastic tip is fitted over gasket 85 to form a chamber 91 leading to a central hole or aperture 92.

In use, the hole 92 is pressed (or sealed) against the skin area to be treated. Abrading particles flowing along channel 82 and in line and coaxial with hole 92 impinge on the skin exposed through hole 92 and the used particles and abraded skin are reflected from the skin and are withdrawn through channel 83.

FIGS. 7, 8 and 9 show a handpiece in accordance with several of the features of the invention. A body 100 of rigid plastic, for example Teflon, has a central axis 101 (FIGS. 8 and 9) and off-center inlet and outlet channels 102 and 103 respectively. Note that these channels are reversed in relative sizes from those of FIG. 4 and are ⅛ inch and ¼ inch respectively.

The body 100 has a very short length, less than about 3 inch and has a reduced diameter threaded end section 105. A sealing O-ring 106 is placed against shoulder 107 between the large diameter and small diameter sections of body 100. A transparent plastic tip 110 is then threaded onto the threaded portion of body extension 105 and compresses O-ring 106 against shoulder 107 to create a seal. The tip 110 forms a vacuum chamber 111 interior spaced from the end of body 100 and has a central aperture 112 (FIGS. 7 and 9) which is about 5/16 inch in diameter and is laterally off-set from the axis of channels 102 and 103.

The novel shortened length of handpiece 100 makes it easier for an operator to manipulate the opening 112 over the skin of a patient. Further, the large output diameter of channel 103 improves the operation of the device and makes it easier to quickly evacuate particles from chamber 111 to ensure against loss of particles to atmosphere if the handpiece is removed from the skin of a subject, breaking the vacuum in chamber 111.

As a further advantage over prior handpieces, the tip 110 can be easily detached and replaced by a new tip after use on a given patient by simply unscrewing the tip and screwing on a new one for the next patient. In the prior art structure of FIGS. 4, 5 and 6, the press fit of tip 90 over seal 85 formed a tight fit making it difficult to remove the used tip and replace it with a new one.

FIGS. 10, 11 and 12 schematically show several novel features for handpiece 31 of FIG. 1 which can be used with the handpieces of FIGS. 4 to 9. In FIG. 10, the tip 32 is shown with a small control opening 119 therein which can be easily closed by the operator's finger to increase the vacuum to produce a more forceful stream of abrasive particles against the skin being abraded when such added force is required. This can be done directly at the handpiece, without requiring the operator to reach for the equipment housing valve 66 in FIG. 1.

It should be further noted that the same result can be obtained by placing the control opening in the body of the handpiece and in communication with either the interior of the tip or the input channel or the output channel.

FIG. 11 shows a modification in which a tube 120 is added to channel 30 in body 33 to extend the point of exit of new abrading particles closer to opening 35 and the skin being treated.

FIG. 12 shows a variation in which the ends of channels 30 and 34 are flared outward at diffuser regions 122 and 123 respectively. It has been found that these diffuser flares tend to prevent clogging of the channels 30 and 34 at their ends entering vacuum chamber 130 formed by tip 31. Note that in prior art handpieces a restriction nozzle has been used at the outlet of channel 30 which has been found to aggravate clogging of the handpiece after a short time.

FIGS. 13 to 16 show a preferred embodiment of a novel disposable plastic tip 200 which contains a central dividing barrier to define air/sand inlet and outlet chambers and FIGS. 17 to 19 describe a preferred handpiece 300 for holding the tip 200.

Referring first to FIGS. 13 to 16, the tip 200 is of clear molded plastic and comprises an outer cylindrical body 201 which extends from a knurled base 202 and having an opening 203 which is coaxial with the central axis of the tip 200. A thread 204 is formed at the interior end of base 202. In accordance with an important feature of the invention, a central barrier 210 extends from the end of chamber 211 (FIG. 15) which receives the handpiece to the apertured end 203 of the tip 200. The end of barrier 210 has a cut-out 212 (FIG. 15) which defines a connection channel adjacent the end of the tip between the two air/sand chambers 213, 214 formed on opposite sides of the barrier 210 (FIG. 14). This novel barrier 210 has been found to substantially increase the volume of airborne sand to the tissue being treated, and the volume being withdrawn therefrom, to and from the handpiece.

FIGS. 17 to 18 show the preferred handpiece body 300 for the tip 200. Handpiece body 300 is a unitary molded body and has an enlarged diameter base 301 from which a smaller diameter integral body portion 302 extends. The base of body portion 302 carries threads 303 which thread into the threads 204 of tip 200, with body portion 302 entering and being fixed within volume 211 (FIG. 15) of tip 200. A gasket can be compressed between the end of tip 200 and the shoulder 304 on base 301 when the tip 200 is threadably fixed to handpiece 300. As in the prior embodiments, a small diameter inlet channel nozzle 310 (0.89 mm diameter) and a large diameter outlet channel nozzle 311 (1.9 mm diameter) are provided. These lead to connection nipples 312 and 313 respectively. Note that when the tip 200 is screwed onto hand piece 300, the barrier 210 should bisect the openings of nozzles 310 and 311.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A handpiece apparatus for skin abrading equipment; said handpiece apparatus comprising:
    a body member elongated in the direction of a central axis and having a removable tip at one end thereof; said removable tip having an outlet opening which is coaxial with said central axis;
    said body member having first and second channels therethrough which are respectively connectable to a first conduit and a second conduit, said first channel and said first conduit being operative to conduct a stream of abrasive particles toward said removable tip and said second channel and said second conduit being operative to conduct said particles and abraded skin away from said removable tip;
    at least a portion of the interior of said removable tip forming a vacuum chamber between an end of said body member and said outlet opening when said outlet opening is sealed against the skin to be abraded;
    and a barrier extending fully across the interior of said removable tip from a position adjacent said outlet opening to a position adjacent the end of said body member to separate the flow of said abrasive particles toward and away from said removable tip.

2. The apparatus of claim 1, wherein said removable tip is connected to said body member by a threaded connection.

3. The apparatus of claim 2, wherein both said first and second channels are laterally displaced from and are on opposite sides of said central axis and are on opposite sides of said barrier.

4. The apparatus of claim 1 wherein said second channel has larger diameter than said first channel.

5. The apparatus of claim 4, wherein both said first and second channels are laterally displaced from and are on opposite sides of said central axis and are on opposite sides of said barrier.

6. The apparatus of claim 1, wherein both said first and second channels are laterally displaced from and are on opposite sides of said central axis and are on opposite sides of said barrier.

7. The apparatus of claim 1 wherein said handpiece has a total length less than about 3 inches.

8. The apparatus of claim 7, wherein both said first and second channels are laterally displaced from and are on opposite sides of said central axis and are on opposite sides of said barrier.

9. The apparatus of claim 1, wherein the end of said barrier adjacent said outlet opening has an arcuate cut out to permit communication from opposite sides of said barrier and across said outlet opening.

10. The apparatus of claim 1, further including a vacuum control element in said hand piece, the vacuum control element being manually adjustable by an operator during use to vary the vacuum pressure.

11. The apparatus of claim 10, wherein the vacuum control element is a bore extending from the exterior to the interior of said removable tip, and positioned to be selectively covered or exposed by the operator during use.

12. The apparatus of claim 1, wherein said barrier is positioned on an extension of said central axis and divides the interior of said removable tip into two equal sized side by side chambers, each being in communication with one of said channels.

13. The apparatus of claim 12, wherein the end of said barrier adjacent said outlet opening has an arcuate cut out that permits communication between said chambers and said outlet opening.

14. The process of abrading skin comprising the steps of;
    producing a flow of abrasive sand taken from a supply reservoir and through a first channel in a handpiece and toward a first interior volume of a removable tip at an end of said handpiece;
    evacuating air from a second interior volume of said removable tip which is laterally adjacent to said first interior volume by a vacuum source connected to a second channel which extends through said handpiece, said first and said second interior volume being in communication with a central opening in said removable tip at an end thereof remote from the handpiece, and separated from each other by a central barrier extending fully across the interior of said removable tip;
    placing said central opening in said removable tip against a surface of the skin to be abraded with both first and second volumes sealed against said skin;
    causing a flow of sand within said removable tip from an end of said first channel and into an end of said second channel, whereby at least a portion of said sand follows a path through said first volume and into said second volume to abrade skin which is exposed to said sand flow through said central opening;
    said handpiece having a length less than about 3 inches whereby an operator can conveniently manipulate the opening over a complex shaped skin surface and can easily keep said opening sealed against said surface.

15. A removable tip for a handpiece used with skin abrading equipment; said removable tip comprising:
    an interior cavity elongated in the direction of a central axis and having an outlet opening coaxial with said central axis at a first end thereof;
    said removable tip being operatively engagable at a second opposite end with a first end of a handpiece;
    the interior cavity being divided into two side by side chambers by a barrier extending fully across said cavity from the first to the second end thereof, but having an opening at the first end of the cavity that provides communication between the two chambers and the outlet opening;
    the handpiece, when operatively engaged with said removable tip, providing communication between said two chambers and respective first and second channels extending through the handpiece, one of said channels being operative to provide a stream of abrasive particles to one of said chambers, and the other of said channels being operative to exhaust particles and abraded skin from the other of said chambers;

said chambers, said communicating channels in said handpiece and said communicating opening in said central barrier providing a flow path for abrasive particles when said outlet opening is sealed against the skin to be abraded whereby said abrasive particles are brought into contact with the skin covering the outlet opening, and are thereafter transported away, together with abraded skin particles.

16. The removable tip described in claim 15, further including a flow control element that is manually adjustable by an operator during use to vary the flow of abrasive particles.

17. The removable tip described in claim 16, wherein the flow control element is a bore extending from the exterior of said removable tip into one of the chambers, and adapted to be covered and exposed by the operator during use.

18. The removable tip described in claim 15, further including a threaded portion at the second end of said cavity for engagement with a threaded portion on the handpiece, the threaded portions on the removable tip and the handpiece being so located that said first and second channels are disposed on opposite sides of said barrier when said removable tip and said handpiece are operatively engaged.

19. The removable tip described in claim 15, wherein the communicating opening in said barrier is an arcuate cut out adjacent to said outlet opening that permits communication between said chambers and said outlet opening.

20. The removable tip claim 15, wherein said barrier is positioned on said central axis so that said chambers are of equal size.

* * * * *